(12) United States Patent
Kobayashi et al.

(10) Patent No.: US 6,645,763 B2
(45) Date of Patent: Nov. 11, 2003

(54) IMMORTALIZED BONE MARROW MESENCHYMAL STEM CELL

(76) Inventors: Naoya Kobayashi, 2033-15, Miyoshi, Okayama-shi, Okayama 703-8261 (JP); Philippe Leboulch, 197 Eighth St., #729, Charlestown, MA (US) 02129; Noriaki Tanaka, 2325-1, Rokujoinnaka, Kamogata-cho, Asakuchi-gun, Okayama 719-0252 (JP); Toshiyoshi Fujiwara, 3-5-30, Higashiyama, Okayama-shi, Okayama 703-8281 (JP)

( * ) Notice: Subject to any disclaimer, the term of this patent is extended or adjusted under 35 U.S.C. 154(b) by 46 days.

(21) Appl. No.: 09/975,304

(22) Filed: Oct. 12, 2001

(65) Prior Publication Data

US 2003/0104615 A1 Jun. 5, 2003

(51) Int. Cl.[7] .................................................. C12N 5/08
(52) U.S. Cl. ..................... 435/366; 435/320.1; 435/455; 435/363; 435/472; 435/372; 435/325
(58) Field of Search ............................. 435/325, 320.1, 435/455, 372, 366, 363

(56) References Cited

U.S. PATENT DOCUMENTS 5,629,159 A * 5/1997 Anderson ........................ 435/6
2002/0022268 A1 * 2/2002 Xu et al. .................... 435/366

FOREIGN PATENT DOCUMENTS

WO      WO 00/18239      4/2000

OTHER PUBLICATIONS

J. Cai et al.; "Construction of a non–tumorigenic rat hepatocyte cell line for transplantation: reversal of hepatocyte cell line for transplantation: reversal of hepatocyte immortalization by site–specific excision of the SV40 T antigen", Journal of Hepatology 2000; vol. 33; pp. 701–708.

K. Westerman et al.; "Reversible immortalization of mammalian cell mediated by retroiral transfer and site–specific recombination"; Pro. Natl. Acad. Sci.; vol. 93, pp. 8971–8976; 1996.

Shi et al.; "Bone Formation by Human Postnatal Bone Marrow Stromal Stem Cells is Enhanced by Telomerase Expression"; Nature Biotechnology, vol. 20, Jun. 2002; pp. 587–591.

J.L. Simonsen et al.; "Telomerase Expression Extends the Proliferative Life–Span and Maintains the Osteogenic Potential of Human Bone Marow Stromal Cells"; Nature Biotechnology, vol. 20, Jun. 2002, pp. 592–596.

Ray, F. A. et al.; "Iterative Chromosome Mutation and Selection as a Mechanism of Complete Transformation of Human Diploid Fibroblasts by SV40 T Antigen"; Carcinogenesis, vol. 14, No. 8, pp. 1511–1516, 1993.

* cited by examiner

*Primary Examiner*—Deborah J. Reynolds
*Assistant Examiner*—Valarie Bertoglio
(74) *Attorney, Agent, or Firm*—Armstrong, Westerman & Hattori, LLP

(57) ABSTRACT

The present invention provides a safe immortalized bone marrow mesenchymal stem cell obtained by transferring a cell proliferation factor gene inserted between a pair of site-specific recombination sequences to a bone marrow mesenchymal stem cell.

1 Claim, 6 Drawing Sheets

(3 of 6 Drawing Sheet(s) Filed in Color)

IMMORTALIZED BONE MARROW MESENCHYMAL STEM CELL

BACKGROUND OF THE INVENTION

The present invention relates to an immortalized bone marrow mesenchymal stem cell obtained by transferring a cell proliferation factor gene into a bone marrow mesenchymal stem cell.

It has been reported by various researchers that bone marrow mesenchymal stem cells differentiate into bone cells, chondrocytes, adipocytes, myocytes, tendon cells, cardiomyocytes. Therefore, it has been expected that if the bone marrow mesenchymal stem cells can be propagated in large numbers in vitro with the pluripotency kept, the resulting bone marrow mesenchymal stem cells will be a very valuable means for regenerative medicine.

As an example other than a bone marrow mesenchymal stem cell, it is known that a cell-line which maintains appropriate functions for differentiation can be produced by transferring an oncogene to BSMC, MDHF or RKC to immortalize each of the cells (K. A. Westerman, et al., Proc. Natl. Acad. Sci., USA., vol 93, 8971, (1996)). If the method is used, it is possible to obtain those immortalized cells in large numbers. However, when each of the immortalized cell-lines is infused into a living body, there is the problem of a possibility that the patient is exposed to unexpected risk of malignant transformation. Therefore, it is difficult to obtain highly safe bone marrow mesenchymal stem cells which can solve such a problem, in large numbers.

The object of the present invention is to provide immortalized bone marrow mesenchymal stem cells which can proliferate indefinitely and have a means to avoid a possibility of malignant transformation.

SUMMARY OF THE INVENTION

As a result of making an intensive study in view of the above situation, the present inventors have found the followings and completed the present invention. The present inventors have found that bone marrow mesenchymal stem cells, which have a means to avoid risk of malignant transformation and can proliferate in large numbers, can be obtained by transferring to bone marrow mesenchymal stem cells a cell proliferation factor gene which is derived from a normal cell and inserted between a pair of site-specific recombination sequences.

Therefore, the present invention provides an immortalized bone marrow mesenchymal stem cell obtained by transferring a cell proliferation factor gene inserted between a pair of site-specific recombination sequences to a bone marrow mesenchymal stem cell.

In the immortalized bone marrow mesenchymal stem cell, the bone marrow mesenchymal stem cell is preferably a human bone marrow mesenchymal stem cell.

In the immortalized bone marrow mesenchymal stem cell, the cell proliferation factor gene is preferably hTERT (human telomerase reverse transcriptase) gene.

In the immortalized bone marrow mesenchymal stem cell, the pair of site-specific recombination sequences is preferably LoxP sequence.

Further, it is preferable that the cell proliferation factor gene is transferred using a retroviral vector.

This file contains color photos.

DETAILED DESCRIPTION

Figure 1:
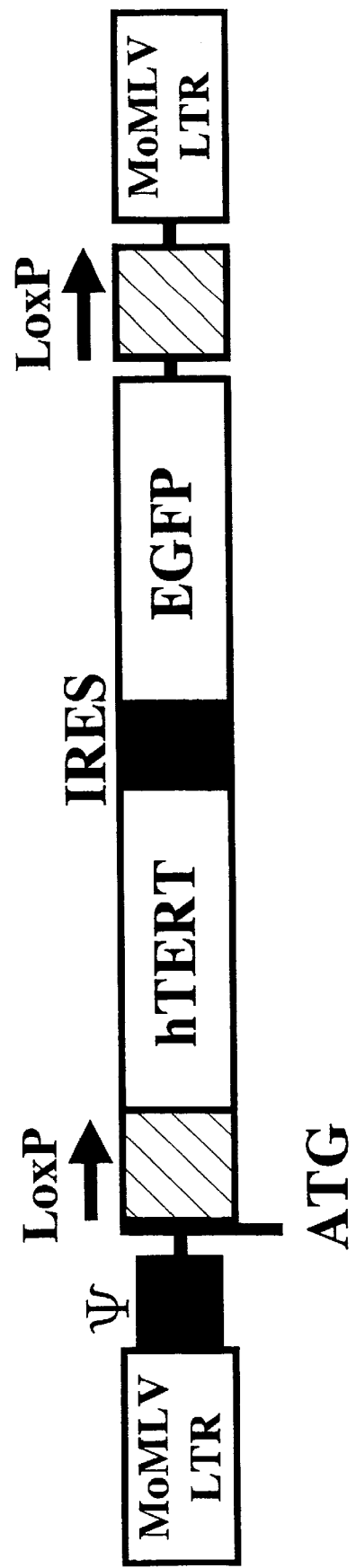
FIG. 1 shows the retroviral vector SSR#197. Herein, ATG denotes initiation codon, ψ denotes a packaging signal, LoxP denotes LoxP sequence, hTERT denotes hTERT gene, EGFP denotes the enhanced GFP gene, MoMLV LTR denotes Moloney murine leukemia virus long terminal repeat, and IRES denotes encephalomyocarditis virus internal ribosomal entry site, respectively.
Figure 2A:
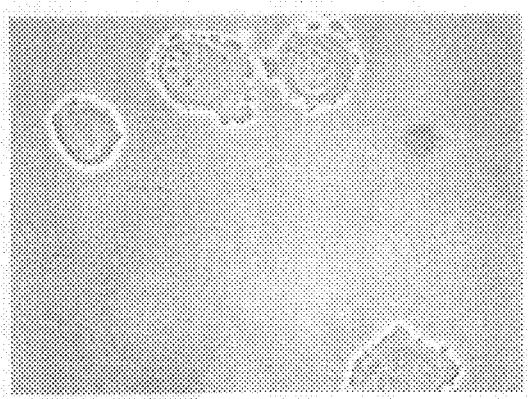
FIG. 2(a) is a phase-contrast photomicrogram of hMSC-2 cells.
Figure 2B:
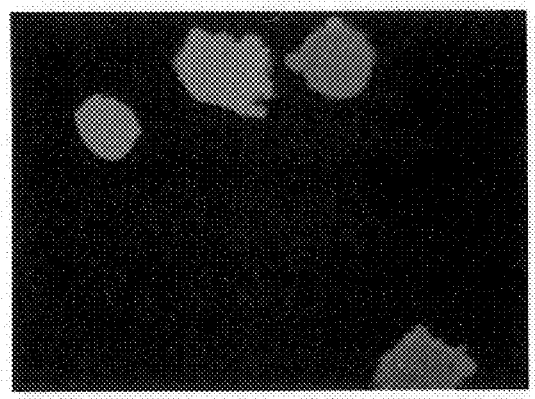
FIG. 2(b) is a fluorescence photomicrogram of hMSC-2 cells shown in FIG. 2(a).

"Bone marrow mesenchymal stem cells" described herein are ancestral cells which can differentiate into bone cells, chondrocytes, adipocytes, myocytes, tenocytes, or bone marrow stromal cells. One example of method for identifying a bone marrow mesenchymal stem cell is a surface antigen test. In the test, a bone marrow mesenchymal stem cell is SH2-, SH3-, CD29- and CD44-positive, but CD14-, CD34- and CD45-negative.

Bone marrow mesenchymal stem cells are the marrow mesenchymal stem cells of, for example, pig, monkey, anthropoid, human and the like. Among them, the human bone marrow mesenchymal stem cells are preferable, and the human adult bone marrow mesenchymal stem cells are the most preferable. The human embryo bone marrow mesenchymal stem cells may also be applied.

A cell proliferation factor gene employed in the present invention is a gene derived from normal cell, and transferring it to a mammalian bone marrow mesenchymal stem cell can make the resulting bone marrow mesenchymal stem cell immortalized. A product from the cell proliferation factor gene is those which essentially relates to cell proliferation and signal transduction in the normal cell. Examples thereof include those which function as growth factor, which have tyrosine kinase activity in the cell membrane, which bind to GTP in the interior of the cell membrane, which have serine/threonine kinase activity in the cytoplasm, and which have the ability to bind to DNA in the nucleus. As such a cell proliferation factor gene, ras gene, myc gene, hTERT gene or the like can be employed. The hTERT gene is preferable, because the expression of the hTERT gene is naturally enhanced in stem and progenitor cells of organs repeating regeneration over lifetime such as blood, skin, intestinal mucosa, endometrium and the like, and in lymphocyte which makes a clonal expansion each time it is exposed to the specific antigen.

In accordance with the present invention, a retroviral vector is used for transferring the cell proliferation factor gene into a bone marrow mesenchymal stem cell. The retroviral vector is used as means for transferring a foreign gene into an animal cell. Since the gene transferred by the retroviral vector is integrated into chromosomal DNA of the host cell, the gene is absolutely transmitted to the daughter cell and therefore can be expressed stably over long period.

As a process to transfer retroviral vectors, intravenous administration, intraperitoneal administration, intraportal administration and administration by direct puncture in case of in vivo, and a process by inoculating retroviral vectors directly on culture cells in case of in vitro are known. The administration by direct puncture and the process by direct inoculating are preferable.

As a process to transfer the retroviral vectors into the culture cells by inoculating the retroviral vectors directly on the culture cells, any process can be used as long as the process achieves the object of the present invention. For example, the transferring can be performed by culturing cells which produce the retroviral vectors, and then inoculating the resulting cultural supernatant on bone marrow mesenchymal stem cells cultured separately. Various conditions such as culture condition and seeding density about each kind of cells can be determined according to the process well known in the art.

In addition, it is preferable that the inoculation on the culture cells is only once, considering effect on the cells such as, for example, stability of chromosomes. However, considering a transferring efficiency of the vectors, it is preferable that the number of the time to inoculate on the cells is more. Based on the facts, it is the most preferable in the present invention to perform 4-hour-infection twice a day, for 3 days in total.

Furthermore, the cell proliferation factor gene used in the present invention is inserted between a pair of site-specific recombination sequences so that the gene can be excised later from the pro-virus transferred into a bone marrow mesenchymal stem cell. "Site-specific recombinant sequence" is a specific base sequence recognized by a site-specific recombinase. In between the specific sequences, homologous recombination comprising the steps of a DNA-strand excision, an exchange of the strands and a coupling thereof are performed. As a site-specific recombinant sequence, there is LoxP sequence, FRT sequence or the like. Among them, the LoxP sequence is preferable. The LoxP sequence is a sequence comprising 34 bases of "ATAACTTCGTATAGCATACATTATACGAAGTTAT" for performing homologous recombination by Cre recombinase alone. When a pair of LoxP sequences inserted in the same direction presents in a same DNA molecule, the DNA sequence inserted therebetween is excised to become a circular molecule (excision reaction).

Further, in the present invention, it is preferable that a selection marker such as GFP gene presents between the pair of site-specific recombinant sequences whenever the cell proliferation factor gene is transferred into the bone marrow mesenchymal stem cell. "Between a pair of site-specific recombinant sequences" means a position inserted between the pair of site-specific recombinant sequences. The GFP gene is used to selectively identify the bone marrow mesenchymal stem cell which is infected with the retroviral vector and wherein a pro-virus is integrated into the genome, by using FACS (fluorescence activated cell sorter). Therefore, a drug-resistance gene may be used instead of the GFP gene as long as the bone marrow mesenchymal stem cell wherein the pro-virus is integrated into genome is identified selectively.

As examples of drug-resistance gene, there is hygromycin resistance gene, neomycin resistant gene, ampicillin resistance gene, *Escherichia coli* gpt gene or the like. It is not particularly limited thereto.

"Immortalized bone marrow mesenchymal stem cell" described herein means a cell that is not tumorigenic, has a shape like a normal bone marrow mesenchymal stem cell, keeps pluripotency of bone marrow mesenchymal stem cell and has a characteristic that it grows in a short term with no need of any special culture condition.

It is preferable that cultivation of the immortalized bone marrow mesenchymal stem cell is carried out under a condition where cell-growth rate is hastened. As a culture vessel, on the other hand, a vessel having no special coating of collagen or the like on the surface is preferable, because it is easy to handle the vessel. A doubling time of the immortalized bone marrow mesenchymal stem cell is from 24 to 72 hours, preferably from 24 to 48 hours, more preferably from 24 to 36 hours. As culture medium for the immortalized bone marrow mesenchymal stem cell, culture medium for mesenchymal stem cells such as mesenchymal stem cell growth medium (catalogue number PT-3001, available from Sanko Junyaku Co., Ltd.) is preferable, and serum-free medium such as CS-C medium is more preferable to be used.

The immortalized bone marrow mesenchymal stem cell of the present invention is a reversible immortalized cell which has a pair of site-specific recombinant sequences. It is possible to remove the transferred cell proliferation factor gene from the immortalized bone marrow mesenchymal stem cell of the present invention by using the site-specific recombinase. Therefore, if the immortalized bone marrow mesenchymal stem cells of the invention are used, it is possible to excise the cell proliferation factor gene from the cells before transplanting them into a living body. Alternatively, it is possible to excise the cell proliferation factor gene from the cells after inducing a differentiation of the immortalized bone marrow mesenchymal stem cells. Both the bone marrow mesenchymal stem cells or cells differentiated therefrom which are obtained by excising the cell proliferating factor gene are very valuable in regenerative medicine, because they have no risk of malignant transformation and they are safe.

The site-specific recombinase is an enzyme which recognizes the site-specific recombinant sequence specifically and performs homologous recombination comprising an excision and coupling, independently. As the site-specific recombinase, there includes Cre recombinase, FLP recombinase or the like. Among them, the Cre recombinase is preferable. The Cre recominase is an enzyme which recognizes the LoxP sequence specifically. It is preferable that the site-specific recombinase is encoded in an adenovirus.

The present invention is more specifically described and explained based on the following Example, Preparation Example and Test Examples, but it is to be understood that the invention is not limited to only them.

Preparation Example
Preparation of Retroviral Vector SSR# 197

Retroviral vector SSR# 197 (see FIG. 1) was prepared according to the conventional method (K. A. Westerman, et al., Proc. Natl. Acad. Sci., USA., vol 93, 8971, (1996)). Concretely, the process is as follows.

1. LXSN retroviral vector was digested with EcoRI and Rsr2. After mutating the EcoRI derived the backbone vector, a polylinker comprising restriction sites (Not1, BamH1, Hind3, EcoR1, Hpa1, Sal1, Sfi1, Cla1 and Rsr2) was inserted into the resultant. Into the Not1/Hind3 site of the resulting vector, a synthesized 511LoxP sequence was inserted. hTERT gene was inserted into the EcoR1/Sal1 site.

2. A cassette vector comprising IRES-GFP, 511LoxP sequence and hepatitis B posttranscriptional regulatory element (T. S. Yen, Mol Cell Biol., 1995) was prepared as follows.

pUC19 was digested with EcoR1 and Hind3. After mutating the EcoR1 derived the backbone vector, a polylinker comprising restriction sites (Xho1, Sal1, EcoRV, Not1, Hpa1, Hind3, EcoR1, Cla1, Sfi1 and Hind3) was inserted into the resultant. Into the Not1 and Hind3 site of the resulting vector, a synthesized 511LoxP sequence was inserted. And then, prepared was a fragment wherein IRES derived from pCITE-Novagen (available from Novagen) and EGFP gene (available from Clontech Inc) were joined at the Nco1 site and the one terminus was a Sal1 site and the other terminus was a blunted Cla1 site. The fragment was inserted into the Sal1 and blunted Bgl2 site of the backbone vector.

3. SSR# 197 vector was completed by inserting the Xho1-and-Cla1 fragment derived from the cassette vector prepared in the above step 2 into the Sal1-and-Cla1 site of the vector prepared in the above step 1.

EXAMPLE 1

Establishment of immortalized bone marrow mesenchymal stem cell line hMSC-2.

The Crip cells producing retroviral vector SSR# 197 (the capacity of the Crip cell to produce retroviral vector SSR# 197, i.e. titer, was $1\times10^5$ cfu/ml) were seeded in a flask T-75 at $1\times10^4$ cells/cm$^2$ of seeding density and then cultured in 15 ml of DMEM+10% NCS (newborn calf serum) medium. When the cell density was about 90%, the medium was exchanged for 15 ml of DMEM+10% NCS medium.

Twenty-four hours after the medium was exchanged, 12 μg/ml of polybrene (available from Sigma) was added to a solution obtained by filtering 15 ml of cultural supernatant of the Crip cells containing the retroviral vector with a filter of a 0.45-μm mesh. The resulting solution was added in exchange for a medium in which $1\times10^6$ cells/cm$^2$ of primary human adult bone marrow mesenchymal stem cells (catalogue number PT-2501, available from Sanko Junyaku Co., Ltd.) had been cultured, to infect the cell for 4 hours. The same infecting procedure was performed twice a day for 3 days in total. After the last infection in each day, the medium was exchanged for flesh CS-C medium and then the bone marrow mesenchymal stem cells were cultured therein.

Two days after the final infection, the cells were treated with trypsin and collected. The GFP-positive cells were then collected by using FACS Calibur (made by Becton Dickinson). hMSC-2 cell line was established by the limiting dilution method (seeding at a half cell/well) using 96-well plates and the mesenchymal stem cell growth medium (catalogue number PT-3001, available from Sanko Junyaku Co., Ltd.). The hMSC-2 cells were observed under a fluorescence microscope (see FIGS.(*a*) and (*b*)).

The hMSC-2 cell had a shape like parent cell thereof and it was immortalized without a crisis of the cease of cell proliferation and grew in one layer in serum-free CS-C medium, and then the number doubled in about 24 hours.

The hMSC-2 cell line was renamed YKNT-12 and deposited as FERM BP-8197 on Sep. 27, 2002, with International Patent Organism Depositary, National Institute of Advanced Industrial Science and Technology, AIST Tsukuba Central 6, 1-1, Higashi 1-Chome Tsukuba-shi, Ibaraki-ken 305-8566 Japan.

Test Example 1
Measurement of Growing Capacity of hMSC-2

Figure 3:
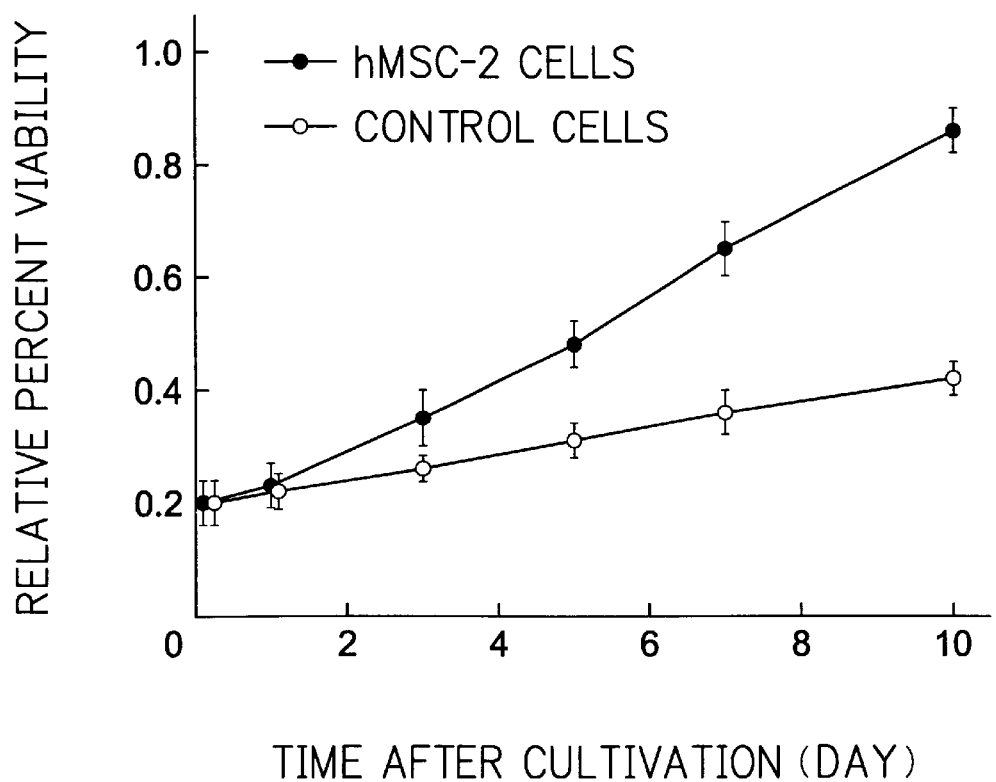
FIG. 3 is a graph showing growth curves of hMSC-2 cells and control cells.

To measure growing capacity of hMSC-2, MTT assay was performed according to a well know method. In the TEST EXAMPLE, bone marrow mesenchymal stem cells wherein there was no transferred hTERT gene were used as control cells.

hMSC-2 cells or the control cells were seeded in 96-well plates at 2000 cells/well. As culture medium, CS-C medium was used. One, three, five and seven day after seeding them, 10 μl of 5-diphenyl-2H-tetrazolium bromide at a level of 20 μg/ml was added to the medium in each well and cultured for 4 hours. Then, 150 μl of isopropanol was added to the resulting medium in each well and the resultant was allowed to react for 10 minutes. After that, the cell growth curve (FIG. 3) was made on the basis of an absorbance ratio of 570 μm to 630 μm using Bio-Rad EIA reader (made by Bio-Rad, Richmond, Calif.).

As a result of the test, it was confirmed that hMSC-2 cells proliferated over PDL (population doubling level) 150. On the other hand, the control cells fell into replicative senescence where cell proliferation ceased at about PDL 25.

Test Example 2
Expression of hTERT Gene in hMSC-2

Expression of hTERT gene in hMSC-2 cells obtained in EXAMPLE 1 was checked by RT-PCR method. As a control, bone marrow mesenchymal stem cells wherein there was no transferred hTERT gene were used. Expression of β-actin gene was checked as a positive control of gene expression in those cells.

RNAzol (available from Cinna/BioTecx, Friendswood, Tex., USA) was used in the RT-PCR method, and RNA was extracted from hMSC-2 cells and 2 μg of the resulting total RNA was reverse-transcribed with RNA reverse transcriptase at 22° C. for 10 minutes and then at 42° C. for 20 minutes according to the protocol.

Figure 4:
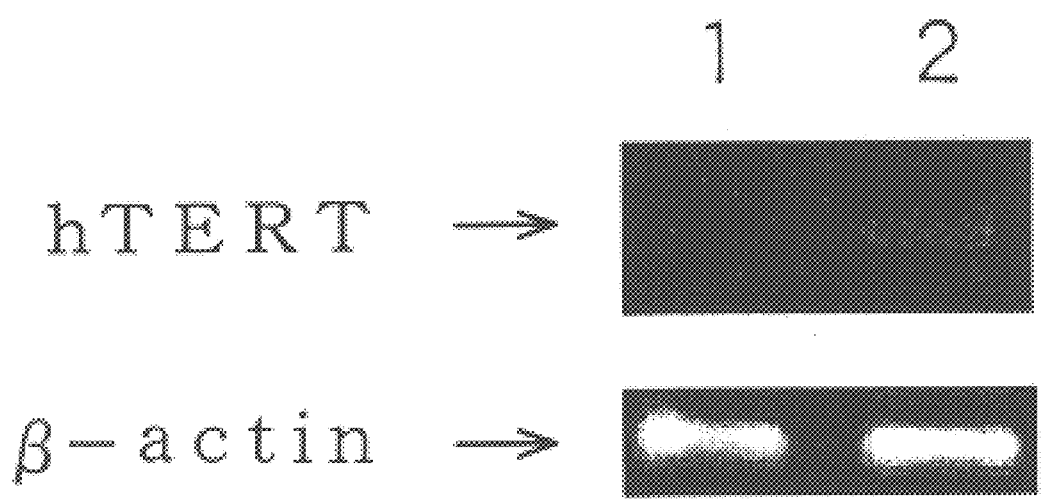
FIG. 4 is a figure showing the result of RT-PCR performed by using hMSC-2 cells and control cells.

The obtained 2 μg of the reverse-transcribed product was applied to PCR amplification using 20 μmol/ml of each primer and AmpliTaq Gold kit (available from Applied Biosystems, Calif., USA) according to the protocol. The PCR was performed as follows: incubation at 95° C. for 10 minutes, 35 cycles of incubation consisting of 95° C. for 30 seconds, 60° C. for 30 seconds and 72° C. for 30 seconds, and final incubation at 72° C. for 7 minutes. As primers for TERT gene or β-actin gene, the following primers were used.

hTERT gene
5' primer: CTGACCAGGGTCCTATTCCA
3' primer: TGGTTATCCCAAGCAAGAGG
β-actin gene
5' primer: TGACGGGGTCACCCACACTGTGCCCATCTA
3' primer: CTAGAAGCATTTGCGGTGGACGATGGAGGG The result of the RT-PCR was shown in FIG. 4. In FIG. 4, the lane 1 denotes the result of the RT-PCR wherein the control cells were used, and the lane 2 denotes the result of hMSC-2 cells. The expressions of hTERT gene and β-actin gene were confirmed in hMSC-2 cells. In the control cells, on the other hand, the only expression of β-actin gene was confirmed. These results show that the transferred hTERT gene was expressed properly in hMSC-2 cells.

Test Example 3
Measurement of Telomerase Activity

To check a telomerase activity in hMSC-2, TRAP assay was performed. In this TEST EXAMPLE, bone marrow mesenchymal stem cells wherein there was no transferred hTERT gene were used as a control.

TRAP assay was performed by using TRAP-ease telomerase detection kit (available from Oncor, Githesbug, Md., USA) according to the protocol. As a result, telomerase activity was positive in hMSC-2 cells but negative in the control cells. These results show that the transferred hTERT gene was expressed and then the resulting hTERT protein has a proper activity in hMSC-2 cells.

Test Example 4
Differentiation of hMSC-2 Cells into Osteoblasts

The hMSC-2 cells established in EXAMPLE 1 were cultured for 21 days using prep kit medium for differentiating osteoblast (product number CL PT-3002, available from Sanko Junyaku Co., Ltd). The medium was exchanged for fresh medium every 5 days.

Figure 5:
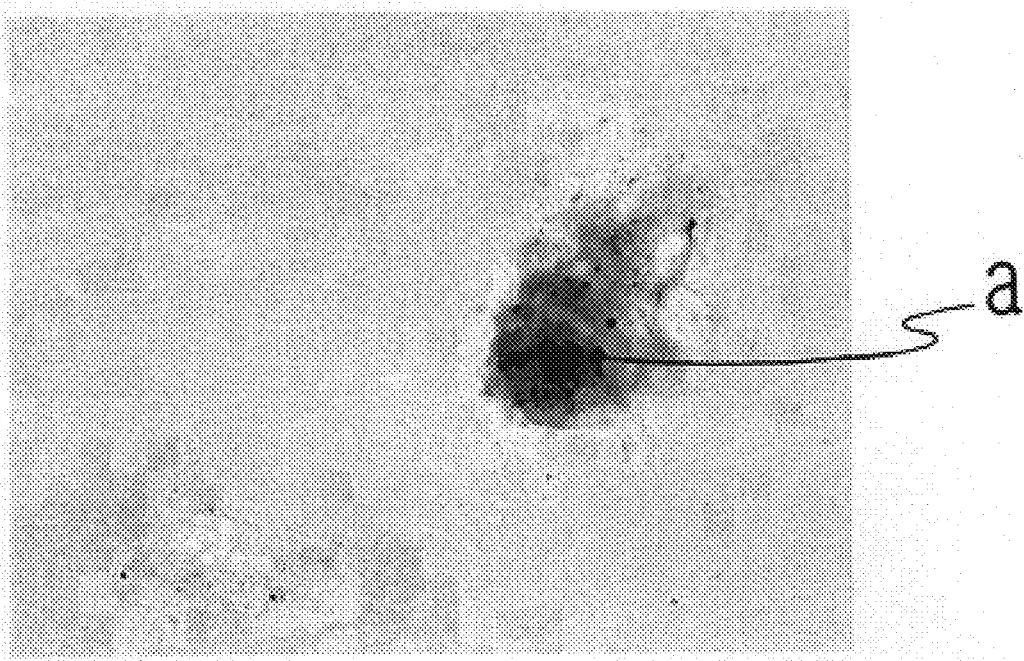
FIG. 5 is a figure showing a part of hMSC-2 cell dyed by Kossa stain.

Then, Kossa stain was carried out according to the conventional method ("Shin Senshokuho no subete", published by ISHIYAKU PUBLISHERS, INC. in 1999). As a result, areas wherein the deposition of calcium had existed were stained blackish brown dots, and then the differentiation into osteoblasts was confirmed (FIG. 5). In FIG. 5, a denotes an area wherein the deposition of calcium had existed, which was stained blackish brown dots.

Test Example 5
Differentiation of hMSC-2 Cells into Adipocytes

The hMSC-2 cells established in EXAMPLE 1 were cultured for 21 days using prep kit medium for differentiating adipocyte (the product number CL PT-3004, available from Sanko Junyaku Co., Ltd). The medium was exchanged for fresh medium every 5 days.

Figure 6:
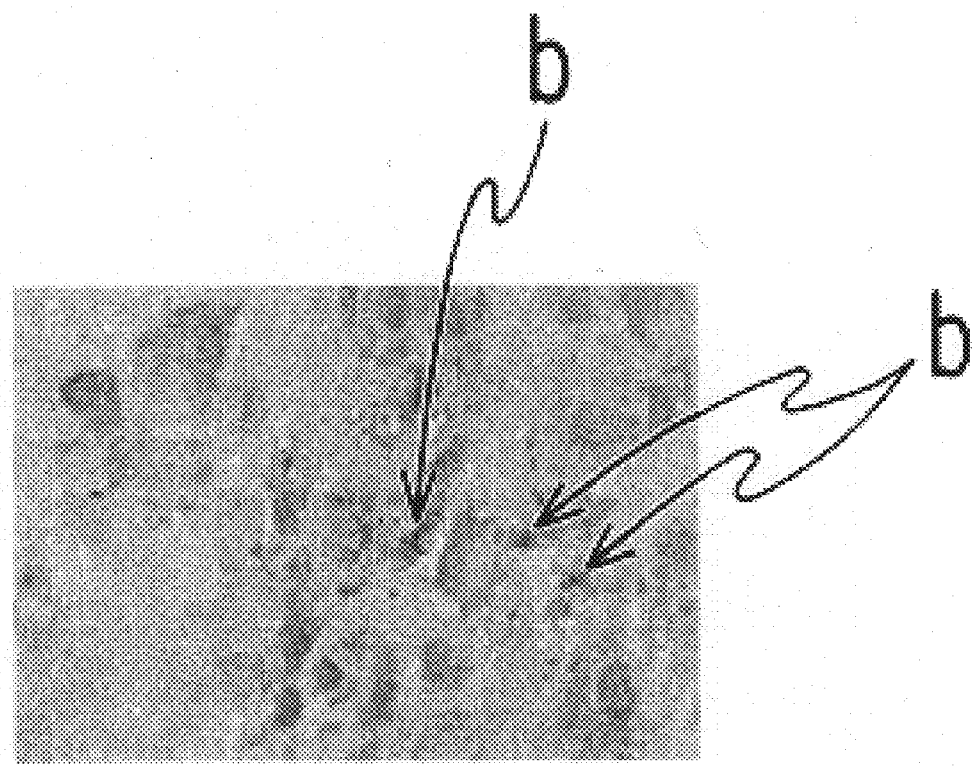
FIG. 6 is a figure showing a part of hMSC-2 cell dyed by Oil red stain.

Then, Oil red stain was carried out according to the conventional method ("Shin Senshokuho no subete", published by ISHIYAKU PUBLISHERS, INC. in 1999). As a result, fat droplets were stained red, so that differentiation into adipocytes was identified (FIG. 6). In FIG. 6, b denotes fat droplets stained red.

Sequence Listing Free Text

SEQ No.1: LoxP sequence
SEQ No.2: 5' primer for polymerase chain reaction to detect hTERT gene
SEQ No.3: 3' primer for polymerase chain reaction to detect hTERT gene
SEQ No.4: 5' primer for polymerase chain reaction to detect human actin gene
SEQ No.5: 3' primer for polymerase chain reaction to detect human actin gene

What is claimed is:

1. An immortalized bone marrow mesenchymal stem cell line deposited as FERM BP-8197.

* * * * *

```
                        SEQUENCE LISTING

<160> NUMBER OF SEQ ID NOS: 5

<210> SEQ ID NO 1
<211> LENGTH: 34
<212> TYPE: DNA
<213> ORGANISM: P1 pharge
<220> FEATURE:
<223> OTHER INFORMATION: LoxP sequence

<400> SEQUENCE: 1
ataacttcgt atagcataca ttatacgaag ttat                              34

<210> SEQ ID NO 2
<211> LENGTH: 20
<212> TYPE: DNA
<213> ORGANISM: Artificial Sequence
<220> FEATURE:
<223> OTHER INFORMATION: 5' primer for polymerase chain reaction to
      detect hTERT gene

<400> SEQUENCE: 2
ctgaccaggg tcctattcca                                              20

<210> SEQ ID NO 3
<211> LENGTH: 20
<212> TYPE: DNA
<213> ORGANISM: Artificial Sequence
<220> FEATURE:
<223> OTHER INFORMATION: 3' primer for polymerase chain reaction to
      detect hTERT gene

<400> SEQUENCE: 3
tggttatccc aagcaagagg                                              20

<210> SEQ ID NO 4
<211> LENGTH: 30
<212> TYPE: DNA
<213> ORGANISM: Artificial Sequence
<220> FEATURE:
<223> OTHER INFORMATION: 5' primer for polymerase chain reaction to
      detect human beta-actin gene

<400> SEQUENCE: 4
```

```
tgacggggtc acccacactg tgcccatcta                                              30

<210> SEQ ID NO 5
<211> LENGTH: 30
<212> TYPE: DNA
<213> ORGANISM: Artificial Sequence
<220> FEATURE:
<223> OTHER INFORMATION: 3' primer for polymerase chain reaction to
      detect human beta-actin gene

<400> SEQUENCE: 5
ctagaagcat ttgcggtgga cgatggaggg                                              30
```